(12) United States Patent
Ertl

(10) Patent No.: US 8,446,595 B2
(45) Date of Patent: May 21, 2013

(54) METHOD AND APPARATUS FOR DETECTING CONTOUR DATA AND/OR OPTICAL CHARACTERISTICS OF A THREE-DIMENSIONAL SEMITRANSPARENT OBJECT

(75) Inventor: Thomas Ertl, Florstadt (DE)

(73) Assignee: Degudent GmbH, Hanau (DE)

( * ) Notice: Subject to any disclaimer, the term of this patent is extended or adjusted under 35 U.S.C. 154(b) by 247 days.

(21) Appl. No.: 13/063,027

(22) PCT Filed: Sep. 11, 2009

(86) PCT No.: PCT/EP2009/061827
§ 371 (c)(1),
(2), (4) Date: Mar. 10, 2011

(87) PCT Pub. No.: WO2010/029163
PCT Pub. Date: Mar. 18, 2010

(65) Prior Publication Data
US 2011/0194121 A1    Aug. 11, 2011

(30) Foreign Application Priority Data
Sep. 12, 2008   (DE) .......................... 10 2008 044 522

(51) Int. Cl.
*G01B 11/24* (2006.01)
(52) U.S. Cl.
USPC ........................................................ 356/610
(58) Field of Classification Search
USPC ...................................... 356/610; 250/559.22
See application file for complete search history.

(56) References Cited

U.S. PATENT DOCUMENTS

| | | | |
|---|---|---|---|
| 5,248,876 A | 9/1993 | Kerstens et al. | |
| 6,697,164 B1 * | 2/2004 | Babayoff et al. | 356/609 |
| 7,092,107 B2 * | 8/2006 | Babayoff et al. | 356/609 |
| 7,230,725 B2 * | 6/2007 | Babayoff et al. | 356/609 |
| 7,259,871 B2 * | 8/2007 | Chen | 356/603 |
| 7,609,875 B2 * | 10/2009 | Liu et al. | 382/154 |
| 7,796,277 B2 * | 9/2010 | Babayoff et al. | 356/601 |
| 2002/0134921 A1 | 9/2002 | Cathey, Jr. | |
| 2004/0252312 A1 * | 12/2004 | Chen | 356/603 |
| 2007/0296959 A1 | 12/2007 | Schwotzer | |

\* cited by examiner

Primary Examiner — Roy M Punnoose
(74) Attorney, Agent, or Firm — Ladas & Parry LLP

(57) ABSTRACT

A method for detecting contour data of a three-dimensional object, where a grid of illumination points of a multi-point illumination is projected onto the object using an optical device and the illumination points are then projected back onto a sensor containing pixels. In order to improve signal-noise ratio and reduce background signal, it is proposed that a grid of illumination points of at least two multi-point illuminations are projected onto the object, that the beams of the illuminating points of are modulated in intensity and that a frequency-selective and/or phase-selective detection is performed of mutually associated first and second illumination points back-projected onto the sensor. The first illumination points derive from a first of the multipoint illuminations and the second illumination points derive from a second of the multipoint illuminations. Differences in intensity and/or frequency of the measurement signals of adjacent pixels of the sensor on which the mutually associated first and second image points are depicted are evaluated for the purposes of determining the contour data.

22 Claims, 5 Drawing Sheets

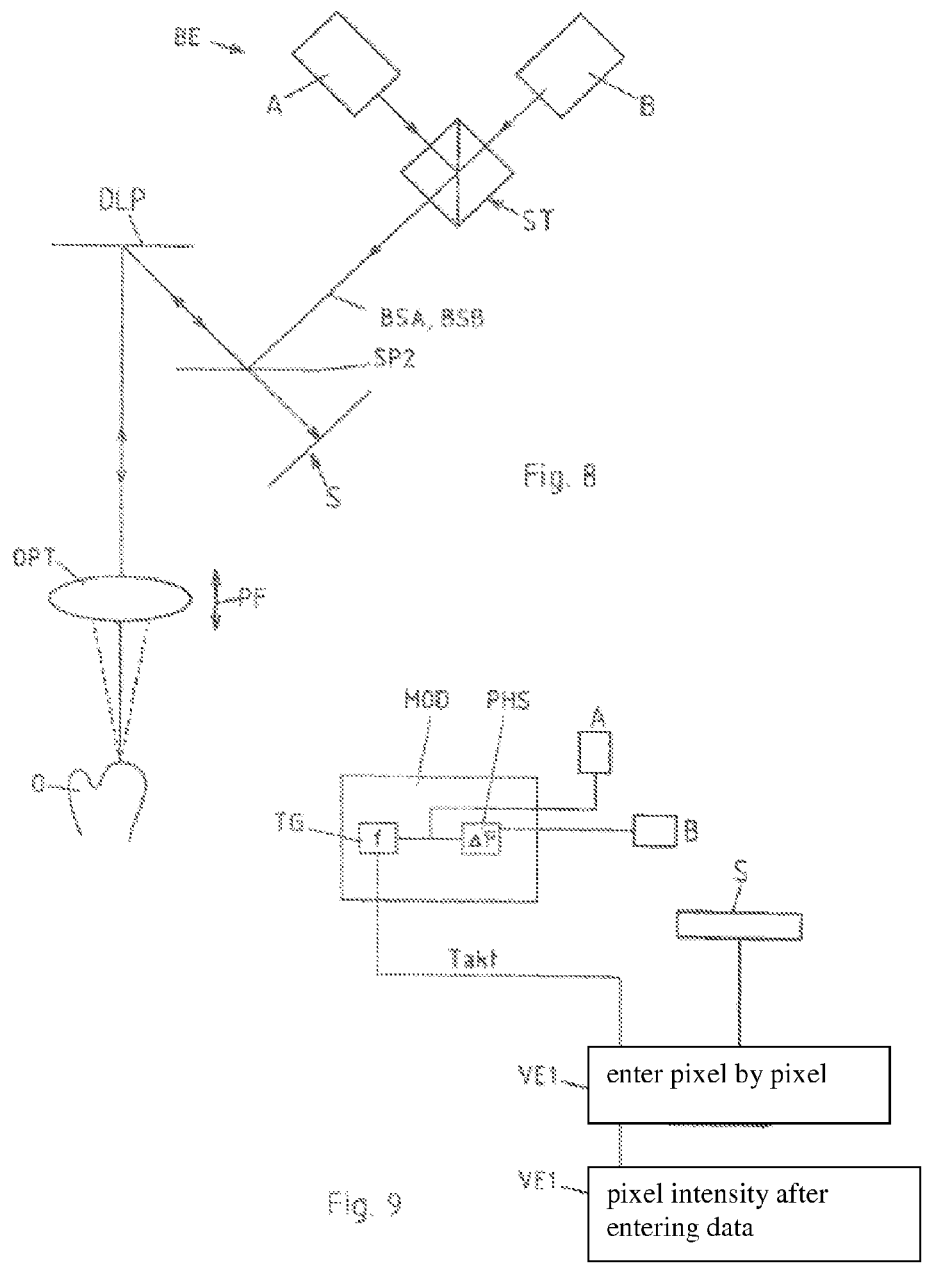

Figure 1:
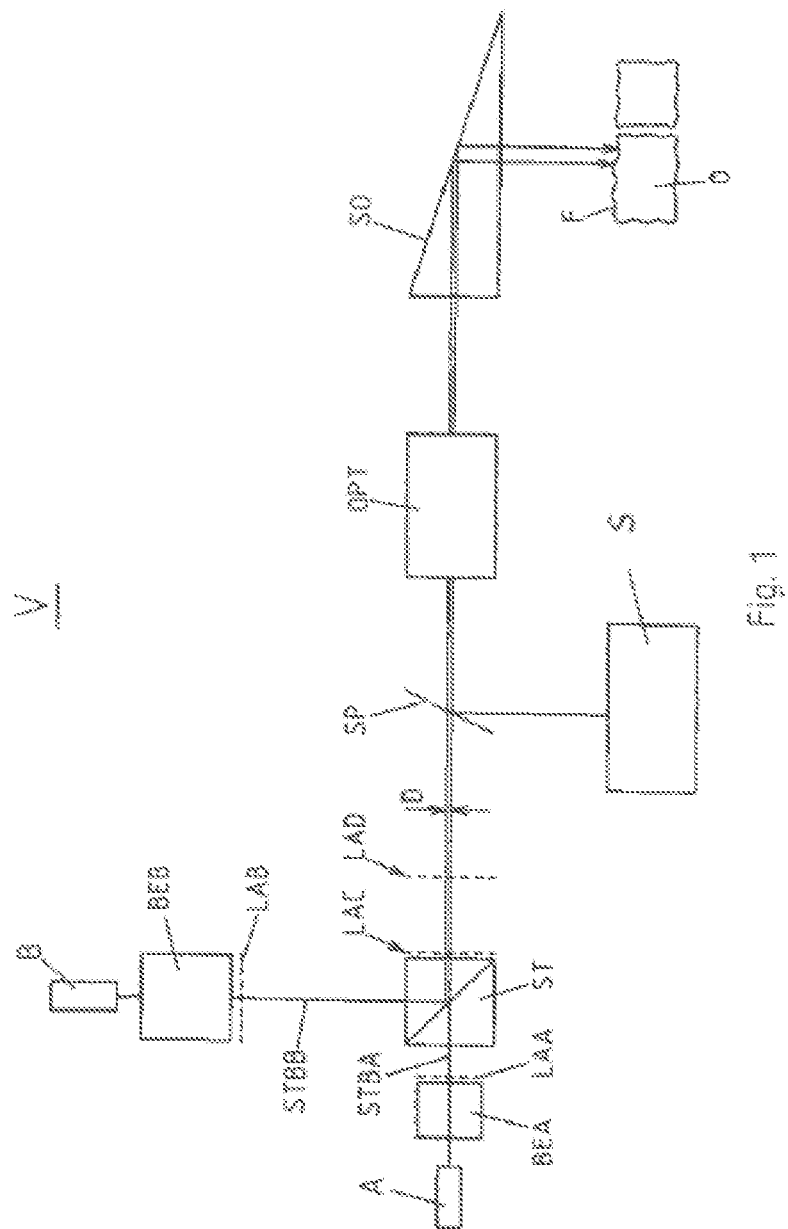

METHOD AND APPARATUS FOR DETECTING CONTOUR DATA AND/OR OPTICAL CHARACTERISTICS OF A THREE-DIMENSIONAL SEMITRANSPARENT OBJECT

The invention relates to a method for acquiring contour data and/or optical characteristics of a three-dimensional semitransparent object, wherein a beam of rays that comprises single light beams is generated from at least one light source for multi-point illumination of the object, which is guided to the object via focusing optics and the emission reflected from the object is acquired by an image sensor that has pixels. The invention relates furthermore to a device for acquisition of contour data and/or optical characteristics of a three-dimensional semitransparent object, in particular a semitransparent object in the dental field such as dentistry or dental restoration, comprising at least one light source for generating a beam of rays which has single beams, focusing optics for guiding the single beams onto the object as well as an image sensor that has pixels, and onto which the reflected emission from the object can be applied.

The invention in particular relates to a method for acquisition of contour data of a three-dimensional object, particularly a semitransparent object, such as a dental object, wherein preferably by means of an optical device preferably for confocal or OCT (optical coherence tomography)—or depth of focus—beam projections, grids of illumination points of a multi-point illumination are projected onto the object and these are then projected back onto a sensor which has pixels.

The subject matter of the invention is also an arrangement for acquisition of contour data and/or optical characteristics of a three-dimensional object, in particular a semitransparent object such as a dental object, comprising a multipoint illumination as well as a sensor that has pixels, wherein between the multipoint illumination and the object and same and the sensor an optical device for preferentially confocal or OCT (optical coherence tomography)—or depth of focus—is arranged, by means of which a grid of illumination points is projected onto the object on the one hand, and on the other the illumination points a projected back onto the sensor.

A method and a device of the type mentioned at the outset is described in WO2006/048164 A2.

In the known method, prior to occurring on an optical beam splitter, the beam of rays is separated into parallel spaced-apart single light beams, wherein the single light beams are at a distance to one another such that the impinging of reflected single light beams onto immediately adjacent pixels of the image sensor does not occur. Interferometry and/or autocorrelation measurement is used with this method, wherein a reference beam is separated from the beam of rays in an optical beam splitter and is reflected by a reference mirror that is movable along the reference beam. By moving the reference mirror, a position of a signal extraction surface can be determined relative to the object.

DE 699 28 453 T2 describes a device to determine one object surface of a dental area. The device comprises a lighting unit for providing an arrangement of incident light beams, which are transmitted by a probe element along an optical path to the dental area in order to generate illuminated points on the area. Light focusing optics are furthermore provided which define one or multiple focal planes from the end face on one position that can be changed by the optics, wherein the focus of each light beam is on one of the focal planes. Furthermore, a translation mechanism is provided for transferring the focal planes relative to the dental area along an axis (Z), which is defined by the propagation of the incident beams.

The emission reflected from the dental area is recorded by a detector, which comprises an arrangement of acquisition elements for measuring the intensity of each of a plurality of imaging light beams which are returning from the points and propagate themselves along an optical path, which is opposite to the ones of the incident beams.

A mirror is arranged moreover in the beam path, which is provided between the lighting unit and the optics focusing the light, wherein the minor has a central aperture and can guide the incident beams in the direction of the optics focusing the light and reflect the imaging light beams to a detector by means of a surface of the minor which surrounds the aperture. The detector is connected with a processor for determining for each light beam a point-specific position, which is the position of the respective focal plane of the one or multiple focal planes, which provide the result of the maximum measured intensity of the reflected light beam, and for generating data based on the point-specific positions which are representative for the topology of the area.

The above described methods have in common that the light is preferably detected from a specific distance (Z-depth). A measurement of the surface profile and/or volume is obtained by traversing the Z-coordinate, i.e. the depth, by means of movable optics.

It is also known from CD/DVD players that a depth selection can also be obtained by means of optics with a high numerical aperture, which quickly de-focuses when one leaves the target Z-depth.

Both full-field illumination with structured light, as in EP 0968687 A2, as well as multi-point illuminations as described in WO2006/048163 A2 and DE 699 28 453 C2 and/or WO00/08415 A1, are used.

The disadvantage of full-field illuminations is a high background signal level, caused by scattering of illumination light within the semi-transparent object, as well as a high requirement of illumination intensity.

The requirement of illumination intensity is significantly lower with multi-point arrangements, but it can also occur that the signal-to-noise ratio is insufficient, and/or the sensitivity to ambient light must be reduced.

EP-A-1 548 481 refers to a confocal microscope which operates with polarized light. The crosstalk between the beams of individual beams of rays should be avoided.

The subject matter of DE-A-10 2005 043 443 is a fluorescence microscope, wherein areas of an object to be measured are excited into different conditions of luminescence.

According to DE-A-197 37 760, three-dimensional structures are to be detected by means of directionally coded wave trains that can be recorded chronologically. For this purpose, the principle of propagation time measurement is used.

The object of the present invention is to further develop a method and a device of the type mentioned at the outset such that an improvement of the signal-to-noise ratio and a reduction of the background signal is achieved. The contour data of the object, such as at least of a tooth or an area thereof, are to be recorded with high accuracy.

This problem is solved by a process in which the intensity of each point of the multi-point illumination is preferably modulated and in which a frequency-selective and, if necessary phase-selective, detection occurs. The modulation occurs preferably by means of a spatially and/or chronologically varying intensity distribution in the immediate local vicinity of a point of measurement and/or a sensor range.

In particular the problem on which the invention is based is solved in that the illumination points of the grids of at least two multi-point illuminations are projected onto the object, that the emissions of the illumination points of the multi-point illuminations are modulated in their intensities and that a frequency and/or phase-selective detection of the first and second reciprocally assigned illumination points that are projected back from the sensor occurs, wherein the first illumination points originate from a first and the second illumination points from at least two multipoint-illuminations, and that for determination of the contour data the differences on which the reciprocally assigned first and second pixels are imaged.

Preferably, in an actually known measuring arrangement (dot-matrix projection onto an object and back projection by means of confocal optics with displacement of the confocal plane, or similar methods such as "depth of focus") each point of a multi-point illumination is modulated in its intensity and its frequency, and a frequency and, if necessary, a phase-selective detection occurs, wherein the modulation occurs by means of a spatially and chronologically varying intensity distribution results in the immediate local vicinity of the measuring point and/or range and therefore the sensor location, and is imaged on the point of measurement and/or range.

For this purpose, preferably at least two illumination sources or light spot grids, which can also include a matrix LCD or DLP (digital light processing) arrangement, are used, wherein the optical axis of the light spot grids can be arranged collinear or at a slight angle to each other. The emissions of the light spot grids can be modulated differently, preferably with a changed phase position.

For reasons of simplification, in the following, the term 'illumination source' can also be used as a synonym for light spot grid, which includes a matrix LCD or DLP arrangement.

In the event of two illumination sources, illumination source A provides an illumination point raster A, and illumination source B an illumination point raster B. In this context, grids A and B are slightly staggered, so that an illumination point from raster A is only at a small distance from its corresponding point from raster B, which is in any case considerably less than the distance to the next pixel of its own dot-matrix. In particular, the spacing between two illumination points of a raster or grid can be in the range between 100 µm to 300 µm, particularly 200 µm, and the spacing of reciprocally assigned illumination points from the rasters and/or grids, which are imaged onto the object lie in a range of 5 µm to 100 µm, preferably between 10 µm and 30 µm, to the extent that it involves a collinear arrangement, i.e. where the beams of the at least two light spot grids run parallel to each other in the direction of the object.

The spacing is the spacing between the center points of the illumination points in the focal plane of the multi-point illumination. The diameter of a sharply defined illumination point should lie between 5 µm and 40 µm. Furthermore, the spacing of the reciprocally assigned pixels of the imaged illumination point rasters or grids is such that no overlapping occurs in the focal plane.

Fundamentally then, if the pixels are sharply defined on the object, the spacing of the center points of the illumination points of a raster should be at least 3 times larger, preferably 3 to 15 times larger than the spacing between two reciprocally assigned pixels.

In other words, the multipoint illuminations are imaged with the pixel rasters that are generated by them to each other such that an illumination point that originates from one of the rasters has a distance to the nearest and thus assigned illumination point of the other raster, which is at least 4 times smaller than the nearest distance from adjacent pixels of each illumination point raster.

During the measurement in the focal plane in a collinear case, the illumination points of the light sources A and B are imaged on different locations (e.g. other pixels of the sensor). But if the measurement is performed out of focus, the illumination points will be imaged blurred and magnified onto the object and therefore the reverse image on the sensor is also blurred.

As a result, adjacent pixels of the sensor also receive light in each case from the respective other illumination source. Because of that, the differences (e.g. with anti-phase modulation) in the signals are less. The maximum signal difference between the adjacent pixels of the sensor is evaluated as indicator for the best focusing in a specific z-distance from the sensor (differential measurement).

In order to determine the respective distance value in the direction of the optical axis (z-axis), the focal plane, i.e. the focal plane along the z-axis is shifted relative to the object. This particularly occurs by adjusting the optics by means of which the illumination point rasters and/or grids and/or the measuring beams are imaged onto the sensor.

According to a further embodiment, the measurement is possible only with an assigned pixel. The one closely adjacent illumination point is imaged "into emptiness" in the focal plane during the measurement, while the other impinges directly onto a pixel. In the defocused case, the now larger diameter of the original illumination point which ran into "emptiness" superimposes the other illumination point and reduces the signal in the event of anti-phase modulation. This may be necessary with sensors that have pixel spacing that is significantly larger than the spacing between the illumination points of the illumination rasters A and B, i.e. the reciprocally assigned illumination points.

In the case of illumination sources that are arranged at a slight angle to each other, one illuminating beam can run coaxial to the direction of measurement, the other intersects the first in the focal plane, or both illuminating beams run at a slight angle to the direction of measurement.

In this case, the illuminating optics can also be configured only weakly focusing or not focusing at all, since in addition to the expansion through defocusing, the spatial position of at least one of the two illumination points also changes depending upon the Z-distance.

Several evaluation possibilities exist:

1. In case of two light sources, the illumination is preferably carried out with half the frequency of the planned detection frequency and preferably at 180° phase shift. Both illuminating beams superimpose in the focal plane and create the detection frequency with the appropriate phase position.

This similarly applies for multiple light sources e.g. ⅓ frequency and 120° phase shift for three light sources, etc.

The illuminating beams diverge outside of the focal plane and the intensity of the detection frequency decreases.

2. With two intersecting beams it can also be determined, for instance, whether the surface to be measured is located above or below the focal plane, because the beams intersect in the focal plane, and therefore the phase position changes at the location of the respective measuring pixel (with reference to an adjacent pixel) when passing through the focal plane. For this purpose, a modulation signal is modulated, e.g. +90° to the reference clock and the other −90° to the reference clock.

According to a further preferred embodiment, preferably individual illumination points or groups of illumination points can be modulated within the illumination raster with different phase position and/or frequency, in order to reduce the crosstalk of the measuring points among one another. This can for instance be done with a DLP (Digital Light Processing® process of the company Texas Instruments) or with an LCoS (Liquid Cristal on Silicon) display. The signal can then be separated into different picture elements according to frequency and phase position, using a reference clock.

The invention teaches that when passing through the focal plane or intersection plane one makes use of the changing crosstalk between adjacent illumination points in order to determine the contour data of the object to be measured. In the case of anti-phase modulation of the emission of the illumination points of the at least two illumination point grids, the maximum signal difference between adjacent pixels of a sensor is utilized in the areas of which an imaged illumination point from the object of the respective light spot grid occurs, wherein the illumination points are reciprocally assigned such that these have a distance in the focal plane that is significantly smaller than the distance of illumination points of each light spot grid.

This type of measurement is particularly used with light spot grids in which the illuminating beams run collinear. If the illumination points do not impinge on the object in the focal plane, then defocusing occurs with the consequence that the intensities of the illumination points that are imaged from the object onto the sensor partially superimpose, i.e. crosstalk occurs, which results in a reduction of the intensity that is determined by means of the pixels. In that case, the local contrast generation and/or its change in closely adjacent areas of the pixels of the sensor is utilized.

When illumination sources and/or light spot grids with beams are used that are arranged at a slight angle to each other, then the focused beams (e.g. laser beams) of the reciprocally assigned illumination points in the focal plane and/or in the intersection point plane defined as the focal plane do not necessarily intersect, so that a signal change of individual pixels and/or the signal difference between the individual pixels to determine the distance C can also be evaluated; because in the intersection point, for instance with illumination sources and/or light spot grids that are anti-phase modulated through which the illumination point raster and/or grid is imaged onto the object, the intensity is zero or virtually zero, if the reciprocally assigned illumination points are clearly defined on the object, provided that the beams are focused. If the focal plane is either in front or behind the object surface, then an intensity results which deviates from that in the intersection point.

Instead of anti-phase modulation, pulse modulation can also be done. This situation also applies for the evaluation of the frequency and/or pulse sequence of the emission impinging onto the pixels of the sensor, in order to determine the Z-distance at which the beams of the reciprocally assigned pixels intersect on the object surface.

With the angled arrangement of the illumination sources and/or light spot grids it is not necessary to utilize defocusing, since the intersection point of the beams and the signals resulting therefrom are used for evaluation.

An arrangement of the type named at the outset is characterized in that the arrangement has at least two multi-point illuminations, that spacing of adjacent pixels between the at least two pixel rasters in the focus plane is smaller than spacing of the pixels in the respective pixel raster.

In this instance, the multipoint illuminations and/or light spot grids created by them can be arranged collinear. But the possibility also exists that the multipoint illuminations and/or the light spot grids are reciprocally arranged such that the beams that are forming the pixels are running inclined to one another.

Irrespective of that, spacing between the pixels in the focal plane of each pixel raster should be between 100 μm and 300 μm, when viewed from pixel center to pixel center, where particularly spacing of the pixels of each pixel raster in the focal plane is 3 to 5 times larger than spacing between reciprocally assigned pixels of the pixel rasters in the focal plane.

It can furthermore be provided that spacing of adjacent pixels of the sensor can be equal or larger than the distance between two reciprocally assigned pixels of the pixel rasters in the focal plane.

Figure 2:
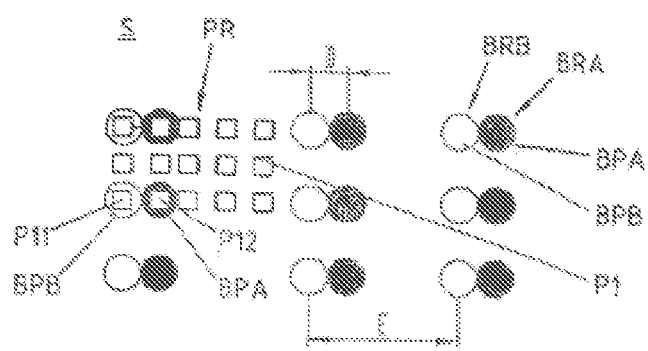
Figure 3:
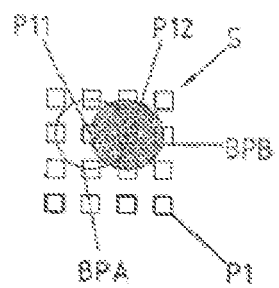
Figure 4:
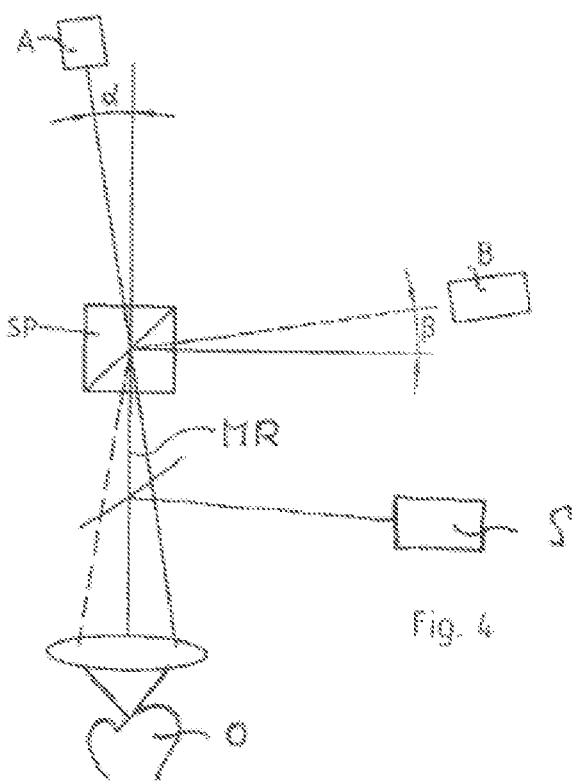
Figure 5:
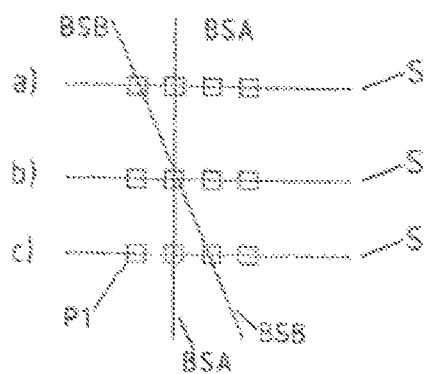
Figure 6:
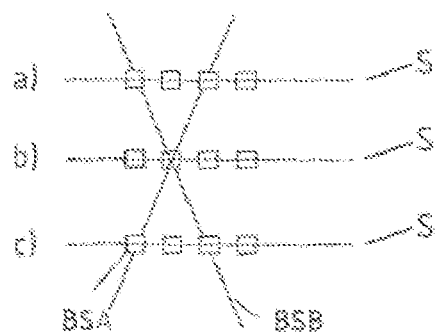
Figure 7:
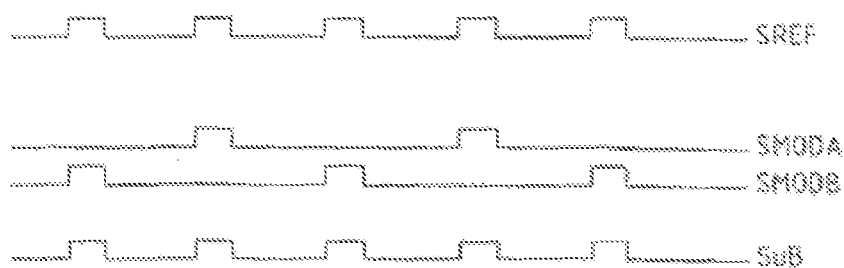

Further particulars, advantages and features of the invention result not only from the Claims, the features to be found in them, either individually and/or in combination, but also from the following description and from the preferred embodiments to be found in the drawing, as follows:

FIG. 1 is a basic design of a device for acquisition of contour data of an object with at least two illumination source which are arranged collinear to each other, FIG. 2 is a schematic representation of the pixel raster of a sensor with illumination points from two illumination rasters, FIG. 3 is a schematic representation of illumination points from two illumination rasters on the pixel raster of the sensor with a collinear arrangement and defocused optics, FIG. 4 is a schematic arrangement of the illumination points with a different angle to the direction of measurement, FIG. 5 a)-c) are schematic representations of the pixel raster of the sensor in side elevation, with angled projection of a first illumination raster and axial projection of a second illumination raster, FIG. 6 a)-c) are schematic representations of the pixel raster of the sensor in side elevation, with angled direction of projection of the first illumination raster and angled direction of projection of the second illumination raster, FIG. 7 is a diagram of clock frequencies for modulation of the illumination rasters as well as a superposition signal, FIG. 8 is a basic design of an alternative device for acquisition of contour data of an object, and FIG. 9 is a schematic design of a modulator for generating modulation signals for the light sources.

FIG. 1 shows a schematic design of a device V for detecting contour data of a free-form surface F of a semitransparent object O like a tooth.

The device comprises two light sources A, B such as laser diodes, the light of which is respectively expanded via a beam expander BEA, BEB and is respectively projected onto a lens array LAA, LAB, as a result of which a beam of rays STBA, STBB of a multitude of parallel single beams is produced, to that a dot-matrix projection of the first and second illumination points occurs on the free surface F of the object O. The single beams are directed via a beam splitter ST, a partially transmitting minor SP, a preferably confocal optics OFT as well as an endoscopic probe element SO onto the object O, so that the first and second illumination points are imaged on it. The reflected single beams also reach the optics OPT and the partially transmitting minor SP via the probe element SO to a detector in the form of a sensor S comprising pixels PI.

As an alternative to the microlens arrays LAA, LAB arranged immediately behind the beam expanders BEA, BAB, a single microlens array LAC can have been developed as a cluster and/or unit with the beam splitter ST. Another alternative is to allocate a common microlens array MLD separately to the beam splitter ST.

According to the embodiment illustrated in FIG. 1, the illumination sources A, B with the beam expander BEA, BEB and the lens arrays LAA, LAB are arranged collinear to each other and are modulated differently, preferably with a changed phase position.

The light sources A, B with the beam expanders BEA, BEB and the lens arrays LAA, LAB are basically forming a light spot grid that can technically also be realized in a different manner. Thus it is possible to use an LCD or DLP (Digital Light Processing) arrangement, for example, for likewise imaging corresponding light spot rasters onto the object O in order to generate the first and second illumination point raster or grid.

In case of two illumination sources A, B, illumination source A supplies an illumination raster BRA and illumination source B an illumination raster BRB, as illustrated in FIG. 2. By this collinear arrangement, the illumination rasters BRA, BRB are illustrated offset parallel to each other. The beams creating the pixels are running parallel to each other. Each run parallel to each other.

Each illumination point raster BRA, BRB consists of individual illumination points BPA as well as illumination points BPB. For this purpose, the illumination rasters BRA, BRB are slightly offset to each other by a distance D, so that an illumination point BPA (first illumination point) of the illumination raster BRA is only at a small distance from its corresponding, i.e. assigned illumination point BPB (second illumination point) of the illumination raster BRB. This distance is at any rate clearly less than a distance E to the next pixel of the own dot-matrix. FIG. 2 furthermore shows a pixel raster PR of a sensor S consisting of individual pixels P.

It is particularly provided that the spacing of the respective illumination points of an illumination raster is between 100 µm and 300 µm and the spacing of the illumination points that are assigned to each other, i.e. of the first and second illumination points, is between 5 µm and 100 µm, preferably between 10 µm and 30 µm. In this instance, the distance is a distance between illumination point center to illumination point center in the focal plane.

FIG. 2 shows that in the collinear case when measuring in the focal plane, the illumination points BPA, BPB of light sources A and B are imaged at different locations, e.g. in other pixels PI1, PI2. FIG. 2 also shows that then when the first and second illumination points, which are reciprocally assigned, are defined sharply on the object, i.e. if the area of the object to be measured is in the focal plane, the illumination points BPA, BPB do not overlap but touch, at the most.

But in case that a defocused measurement is performed, i.e. when the area of the object O on which the first and second reciprocally assigned illumination points BPA, BPB are imaged, does not lie in the focal plane, the illumination points BPA, BPB are imaged blurred and magnified onto the object and therefore also reimaged blurred onto the sensor S. In this way, adjacent pixels PI1, PI2 of sensor S also each receive light from the respective other light source A, B. As a result, the differences, e.g. during anti-phase modulation, are smaller in the signal (see FIG. 3).

In this case, the maximum signal difference between adjacent pixels PI1, PI2 of sensor S is used as indicator for the best focusing in a specific Z-distance between object O and sensor S (differential measurement).

FIG. 4 shows an embodiment in which the illumination source A is arranged at an angle α to the direction of measurement MR and the illumination source B at an angle β to the direction of measurement MR. In case of two illumination sources B that are arranged slightly angled to each other, an illuminating beam BSA can run coaxially to the direction of measurement MR, wherein the illuminating beam B runs at an angle to the illuminating beam A.

Alternatively, both illuminating beams BSA and BSB can run at a slight angle to the direction of measurement MR.

FIGS. 5a) to 5c) provide a view onto the sensor S from the side, presuming that the object O to be measured pursuant to FIG. 5a) is above the adjusted focal plane, pursuant to FIG. 5b) is in the adjusted focal plane, and pursuant to FIG. 5c) is below the adjusted focal plane, respectively.

FIGS. 6a) to 6c) also show pixel rasters of the sensor S as a side elevation, where the object pursuant to FIG. 6a) is above the focal plane, pursuant to FIG. 6b) is within the focal plane, and pursuant to FIG. 6a) is below the focal plane.

In the above-mentioned cases, the illuminating optics can also be configured only weakly focusing or not focusing at all, since in addition to the expansion through defocusing also the spatial position of at least one of the two illumination points changes in dependence of the Z-distance.

From FIGS. 5 and 6 it is apparent that when the beams that are aligned tilted to each other, which form the first and second illumination points, intersect, the measuring location and/or measuring point then lies on the object surface F in the focal plane. This is how the arrangement is configured.

This intersection point is correspondingly projected back onto the sensor. In this event, the measuring signal of the respective pixel is determined by the two reciprocally assigned pixels. Illumination points are not imaged onto the immediately adjacent pixels. Consequently, the measuring signal difference of adjacent pixels is likewise evaluated in order to determine the distance (Z-axis) to the object.

A prerequisite for this type of evaluation is that the spacing between two pixels is smaller than the spacing between the pixels of an image raster and therefore also the spacing between a pair of reciprocally arranged first and second pixels. The arrangement should furthermore be optically or mathematically configured so that the intersection point of two beams that generate the reciprocally assigned illumination points is in the focal plane of the sensor.

Several evaluation possibilities are possible:

In the case of two light sources A, B and/or light spot grids, which can also be formed through LCDs or DLPs, for example, the illumination is performed with half the frequency of the planned detection frequency and 180° phase shift. In the focal plane pursuant to FIG. 5b and/or FIG. 6b both illumination beams BSA, BSB are superimposed and create the detection frequency with a corresponding phase position, as shown in FIG. 7. FIG. 7 shows the reference signal SREF, a modulation signal SMODA for illumination raster BRA, a modulation signal SMODB for the illumination raster BRB, as well as a superposition signal SÜB.

This applies similarly for several light sources, for example one third frequency and 120° phase shift for three light sources etc. Outside of the focal plane, the illumination beams BSA, BSB diverge and the intensity of the detection frequency decreases (see illustration in FIGS. 5a), c) and 6a), c)).

A further evaluation possibility is to determine for two intersecting beams BSA, BSB, for instance, whether the surface to be measured is located above or below the focal plane, because the beams intersect in the focal plane and therefore the phase position changes at the location of the respective measuring pixel PI, with reference to an adjacent pixel, when passing through the focal plane. For this purpose, a modulation signal is modulated, e.g. +90° to the reference clock and the other −90° to the reference clock.

Furthermore the possibility exists to modulate groups of illumination points and/or individual illumination points within an illumination raster BRA, BRB with different phase position or frequency, in order to reduce the crosstalk of the measuring points among one another. This can for instance be done with DLP (Digital Light Processing—a process of Texas Instruments) or with LCoS (Liquid Cristal on Silicon) display. In this case, the detector signal for the different pixels can be separated according to frequency and phase position, using a reference clock. A schematic representation of an embodiment is shown in FIG. 8.

FIG. 8 shows an illumination device BE, as was previously explained with reference to FIG. 1. The illumination beams BSA, BSB that are emitted from the illumination device BE impinge on a partially transmitting minor SP2 and are imaged onto the object O via a DLP (Digital Light Processing) and movable optics. The focus plane can be adjusted by moving the optics along in the direction of the arrows PF. The beams reflected from the object O are detected by the sensor S like CMOS or CCD sensor.

FIG. 9 finally shows a modulator MOD for the modulation of the light emitted by the light source A and/or light source B. For this purpose, one output of a clock generator TG is directly connected with a control input of the light source A and via a phase shifter PHS with one control input of the light source B. A further output of the clock generator TG is connected with a processing unit VE1, in which the pixels PI of the sensor S are entered pixel by pixel. Thereafter, the pixel intensity is balanced with a clock pulse in a further processing unit VE 2. At the same time, phase and frequency selection is possible.

The invention teaches that the crosstalk is specifically used so that it can be brought about from two reciprocally assigned pixels that are imaged onto the sensor from the object O. For this purpose in a collinear arrangement and anti-phase modulation of the emissions which create the first and/or the second pixels, maximum intensity difference of adjacent pixels and/or pixel areas are utilized by means of which the measuring signals that are projected back from the pixels are generated.

To the extent that the beams that are creating the pixels run inclined towards each other, precise data about the surface data of the object to be measured can likewise be collected from the deviations in the intensity and/or in the frequency. For this purpose it is not mandatory to use the characteristics of the defocusing, so that also a laser radiation can be used, for example, because the intersection points from which the beams that are creating the illumination points are evaluated.

Furthermore there is a possibility that optical characteristics such as wavelength-dependent transparency can be derived from the measuring data, to the extent that a spectral evaluation occurs.

The invention claimed is:

1. Method for acquisition of contour data of a three-dimensional object, in particular of a semitransparent object, such as a dental object, wherein preferably by means of an optical device preferably for confocal or OCT (optical coherence tomography)—or depth of focus—beam projections, grids of illumination points of a multi-point illumination is projected onto the object and these are then projected back onto a sensor which has pixels, characterized in that rasters of illumination points from at least two multi-point illuminations are projected onto the object, that the emissions of the illumination points of the multi-point illuminations are modulated in their intensities and that a frequency and/or phase-selective detection of the first and second reciprocally assigned illumination points that are projected back onto the sensor occurs, wherein the first illumination points originate from a first and the second illumination points from a second of the at least two multipoint-illuminations, and that for the determination of contour data differences of intensity and/or frequency of the measuring signals of adjacent pixels of the sensor are evaluated, onto which the reciprocally assigned first and second pixels are imaged.

2. Method according to claim 1, characterized in that a first and a second multi-point illumination are used, which respectively image a pixel grid and/or pixel raster onto the object, in which the spacing of reciprocally assigned first and second illumination points is smaller than the spacing of the first and/or second illumination points in the respective pixel grid and/or pixel raster in the focal plane.

3. Method according to claim 1, characterized in that spacing between the adjacent first pixels and/or adjacent second pixels in the focal plane is selected is at least three times larger than spacing between a first pixel and second pixel that is assigned to it.

4. Method according to claim 1, characterized in that the spacing of adjacent first and/or second pixels when viewed between their center points in the focal plane is determined such that it is approximately between 100 μm and 300 μm.

5. Method according to claim 1, characterized in that the modulation of the emission and/or emissions and the imaging of the pixel grids and/or pixel raster onto the object occurs such that a spatial and/or chronologically changing intensity distribution in the immediate local vicinity of at least one pixel of the image sensor occurs.

6. Method according to claim 1, characterized in that the emissions of the at least two multi-point illuminations are modulated anti-phase and that for the determination of the contour of the object the maximum signal difference between adjacent pixels of the image sensor are evaluated, in the area of which a first and a second pixel that is assigned to it are imaged in each case.

7. Method according to claim 1, characterized in that the at least two multi-point illuminations are arranged collinear.

8. Method according to claim 1, characterized in that the beams creating the first and second pixels of the at least two multi-point illuminations are running inclined and/or at an angle to one another.

9. Method according to claim 8, characterized in that at least one of the at least two multi-point illuminations runs inclined to the direction of the measuring beam.

10. Method according to claim 8, characterized in that the at least two multi-point illuminations are arranged reciprocally angled to the direction of the measuring beam.

11. Method according to claim 1, characterized in that with multi-point illuminations on which the beams impinging on the object are running at an angle to each other, optics are used which are configured weakly focusing or not focusing.

12. Method according to claim 1, characterized in that the spacing between a pair of reciprocally assigned first and second illumination points to the spacing of the pixels of the sensor is selected such that with measurements in the focal plane the first illumination points are impinging on pixel-free areas of the image sensor and the second illumination points impinge on a pixel of the image sensor and that during defocusing both the first as well as the second illumination points impinge on pixels.

13. Method according to claim 1, characterized in that during use of n-light sources for generating of corresponding multi-point illuminations, emission of each light source with reference to the other light sources has a phase shift of 360°/n and/or emission of each light source has a frequency v/n with v=detection frequency.

14. Method according to claim 1, characterized in that by changing the phase position it can be determined from the signal of a pixel whether the measuring point on the object is in, on, or below the focal plane.

15. Method according to claim 1, characterized in that the contour data of the object are determined from the type of the crosstalk from the measuring signals created from the reciprocally assigned first and second pixels.

16. Method according to claim 1, characterized in that the measuring signals for the determination of optical characteristics are spectrally evaluated.

17. Arrangement for acquisition of contour data and/or optical characteristics of a three-dimensional semitransparent object (0), in particular a semitransparent object such as a dental object, comprising a multi-point illumination (LAA, LAR) as well as a sensor (S) comprising pixels (PH, PI2), where between the multi-point illumination and the object and this said object and the sensor an optical device is arranged preferably for confocal, OCT or depth of focus beam projections, by means of which on the one hand a raster of illumination points (BRA, BRB) is projected from the multi-point illumination onto the object, and on the other hand the illumination points are projected back onto the sensor, characterized in that the arrangement comprises at least two multi-point illuminations (LAA, LAB), and in that spacing of adjacent pixels between the at least two pixel rasters (BRA, BRB) in the focal plane is smaller than spacing of the pixels in the respective pixel raster, wherein for determining the contour data differences of intensity and/or frequency, measuring signals of adjacent pixels of the sensor are evaluated, onto which the reciprocally assigned first and second pixels are imaged, which originate from different pixels rasters, and spacing of the pixels of each pixel raster (BRA, BRB) in the focal plane is at least three times larger than spacing between adjacent reciprocally assigned pixels of the pixel rasters in the focal plane.

18. Arrangement according to claim 17, characterized in that the multi-point illuminations (LAA, LAB) are arranged collinear.

19. Arrangement according to claim 17, characterized in that the multi-point illuminations (A,B) are arranged to each other such that the beams that are forming the axles run inclined towards each other.

20. Arrangement according to claim 17, characterized in that spacing between the pixels in the focal plane of each pixel raster (BRA, BRB) is between 100 μm and 300 μm, when viewed from pixel center to pixel center.

21. Arrangement according to claim 17, characterized in that spacing of the pixels of each pixel raster (BRA, BRB) in the focal plane is at least 3 preferably up to 15 times larger than spacing between reciprocally assigned pixels of the pixel rasters in the focal plane.

22. Arrangement according to claim 17, characterized in that spacing of adjacent pixels (PI1, PI2) of the sensor (S) is the same as or larger than spacing between two reciprocally assigned pixels of the pixel rasters (BRA, BRB) in the focal plane.

* * * * *